(12) United States Patent
Holohan

(10) Patent No.: US 11,435,357 B2
(45) Date of Patent: Sep. 6, 2022

(54) SYSTEM AND METHOD FOR DISCOVERY OF GENE-ENVIRONMENT INTERACTIONS

(71) Applicant: Genteract Corporation, Phoenix, AZ (US)

(72) Inventor: Brody Holohan, Phoenix, AZ (US)

(73) Assignee: GENTERACT CORPORATION, Phoenix, AZ (US)

( * ) Notice: Subject to any disclaimer, the term of this patent is extended or adjusted under 35 U.S.C. 154(b) by 316 days.

(21) Appl. No.: 15/888,005

(22) Filed: Feb. 3, 2018

(65) Prior Publication Data

US 2020/0371111 A1  Nov. 26, 2020

(51) Int. Cl.
| | | |
|---|---|---|
| *G01N 33/68* | (2006.01) | |
| *G16B 30/00* | (2019.01) | |
| *G16B 15/00* | (2019.01) | |
| *G01N 33/50* | (2006.01) | |
| *G16B 20/40* | (2019.01) | |
| *G16B 20/00* | (2019.01) | |
| *G16B 50/00* | (2019.01) | |

(52) U.S. Cl.
CPC ..... *G01N 33/6803* (2013.01); *G01N 33/5008* (2013.01); *G16B 15/00* (2019.02); *G16B 20/00* (2019.02); *G16B 20/40* (2019.02); *G16B 30/00* (2019.02); *G16B 50/00* (2019.02)

(58) Field of Classification Search
CPC .......... G01N 33/6803; G01N 33/5008; G16B 15/00; G16B 20/00; G16B 20/40; G16B 30/00; G16B 50/00
See application file for complete search history.

*Primary Examiner* — Jerry Lin
(74) *Attorney, Agent, or Firm* — Baker Botts L.L.P.

(57) ABSTRACT

A system and method for detecting gene-environment interactions, a method of making predictions about individual response to a specific environmental factor with respect to a single phenotype and a simulation method determining the optimal parameters for use of the gene-environment interaction detection method. Gene-environment interaction detection and the discovery of previously unknown interactions are facilitated.

21 Claims, 12 Drawing Sheets

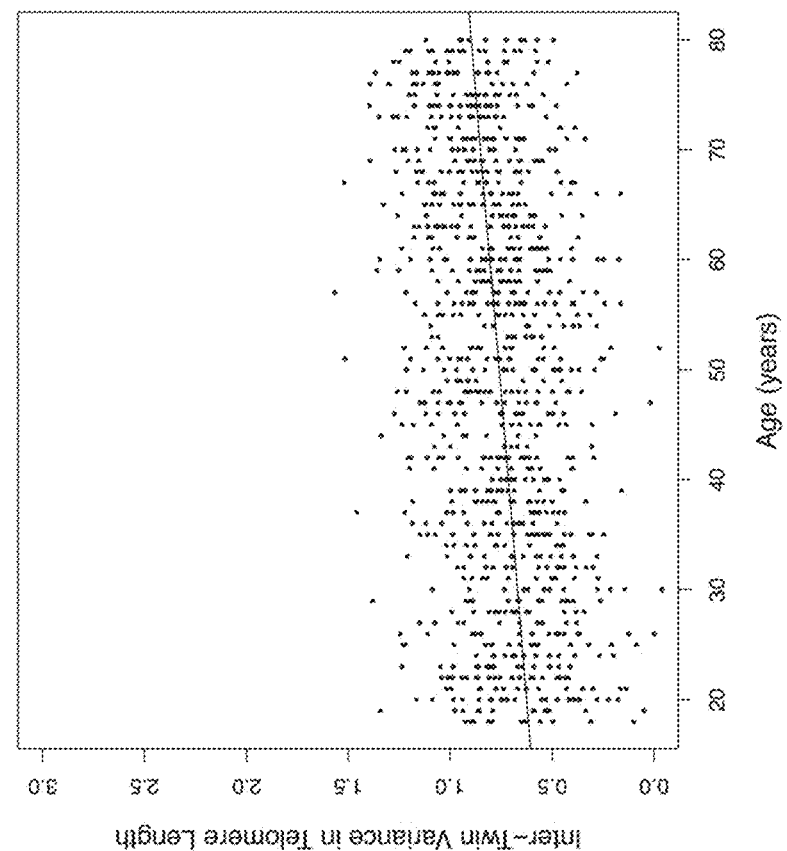
Fig. 2C  Inter-Twin Variance in Telomere Length vs. Age in Monozygotic Twins
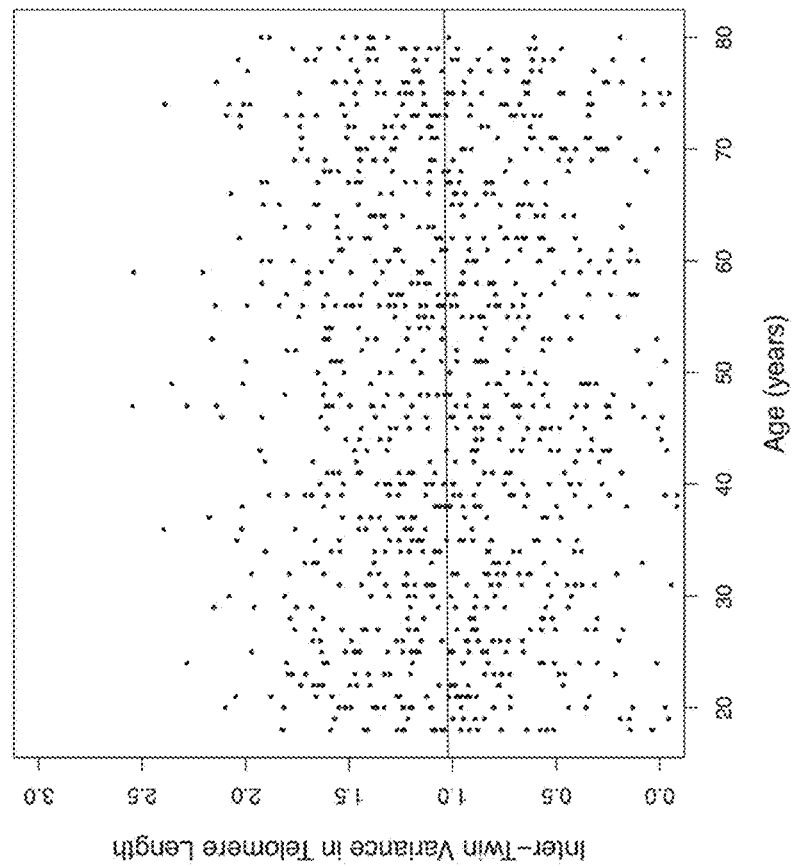
Fig. 2B  Inter-Twin Variance in Telomere Length vs. Age in Dizygotic Twins

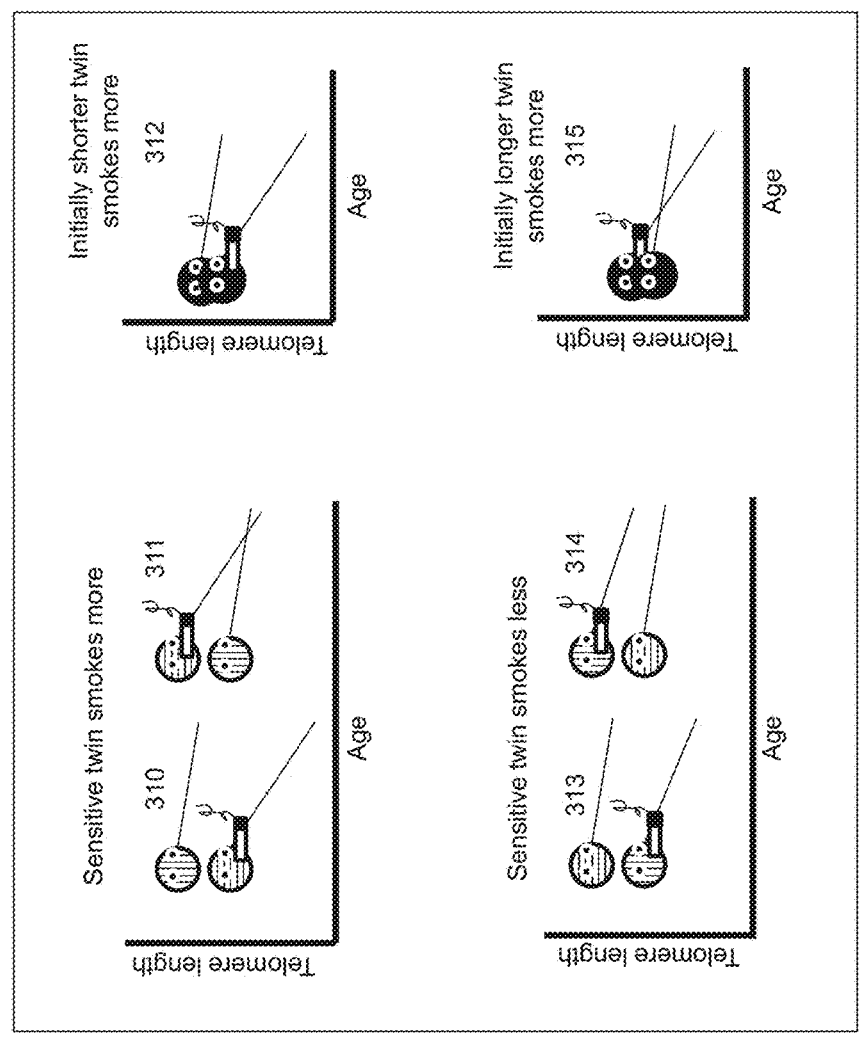

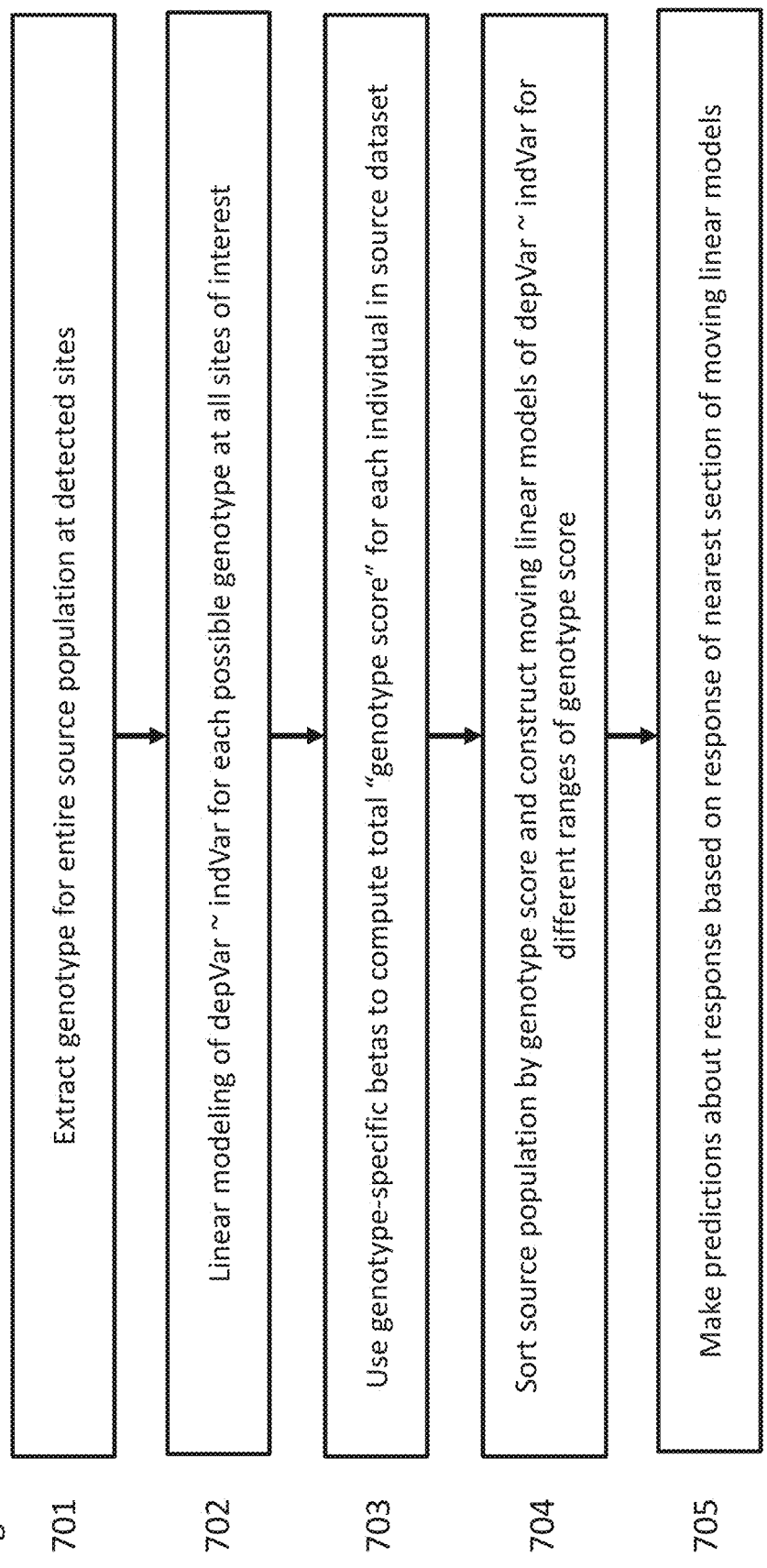

Fig. 7

701 Extract genotype for entire source population at detected sites

702 Linear modeling of depVar ~ indVar for each possible genotype at all sites of interest 703 Use genotype-specific betas to compute total "genotype score" for each individual in source dataset 704 Sort source population by genotype score and construct moving linear models of depVar ~ indVar for different ranges of genotype score 705 Make predictions about response based on response of nearest section of moving linear models

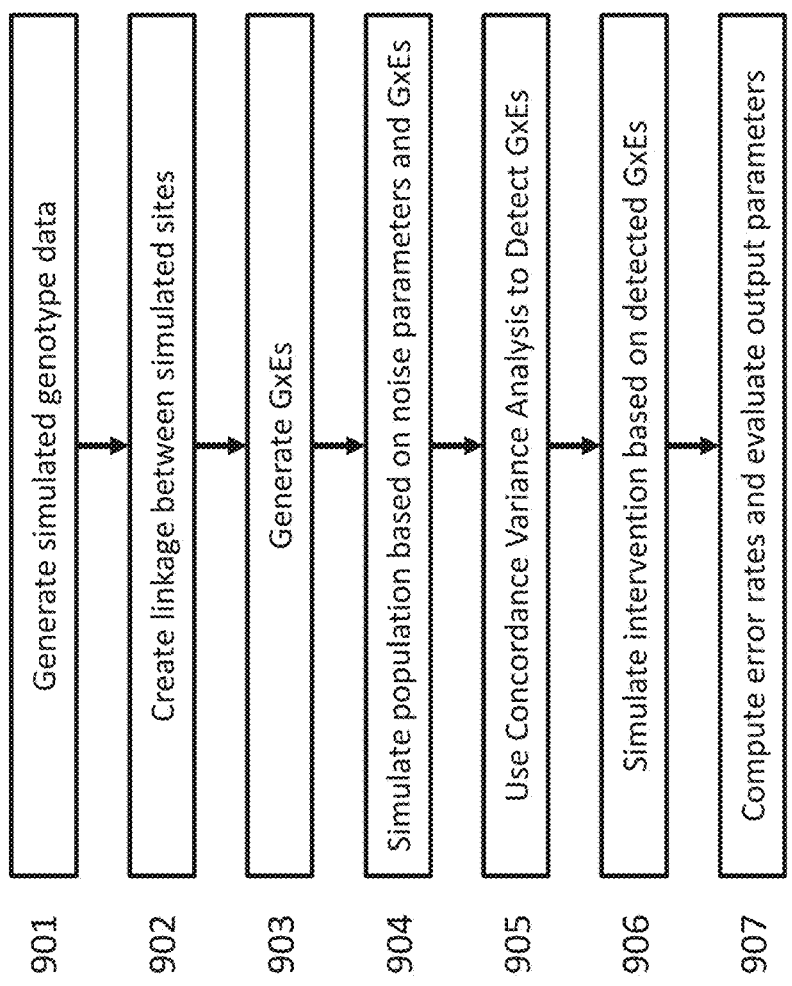

Fig. 9A

901 Generate simulated genotype data
902 Create linkage between simulated sites
903 Generate GxEs
904 Simulate population based on noise parameters and GxEs
905 Use Concordance Variance Analysis to Detect GxEs
906 Simulate intervention based on detected GxEs
907 Compute error rates and evaluate output parameters

Fig. 9B

| | |
|---|---|
| Number of sites | 500 |
| Number causal | 10 |
| Mean linked sites | 3 |
| Population size | 2000 |
| Effect SD | 0.5 |
| Intervention Size | 10 |
| Intervention SD | 5 |
| Proportion compliant | 0.9 |
| Number of comparisons | 45000 |
| Noise SD | 2 |

SYSTEM AND METHOD FOR DISCOVERY OF GENE-ENVIRONMENT INTERACTIONS

BACKGROUND OF THE INVENTION

Field of the Invention

The present invention relates generally to the field of genetics, more specifically to genetic analysis, especially regarding the interactions between genetics, the environment, and biological systems, often called "Gene-Environment Interactions" (GxEs). In particular, the invention includes a method of detecting GxEs in source data.

Description of Prior Art

A number of existing methods to detect GxEs exist. One commonly used method is the PLINK whole genome analysis toolset. PLINK and most other such methods look for a difference between the regression coefficients of two variables with respect to a single dependent variable. Specific application of these methods for GxEs generally utilize a binned version of the dependent variable, "affected" and "not affected", for example, and then look for an association between a continuous or factor predictor variable and different genomic positions. Each association detected is considered individually, and any predictions made by the results are not typically evaluated in the context of other findings.

Key features of existing GxE detection methods include:

A. Use of a binned dependent variable to categorize individuals in the source dataset into two or more clearly-demarcated groups.

B. Use of the primary dependent variable information rather than any derived or computed values for GxE detection.

C. Comparison of regression coefficients of the dependent variable against the two independent variables to look for a statistically significant interaction of the independent variables.

These methods sacrifice a great deal of statistical power for most uses because they force the user to bin the data into two or more clearly-demarcated groups to make the analysis possible. This binning is often ad hoc, and may yield spurious results as a consequence of users tweaking the parameters of the binning such that the results are consistent with their propter hoc assumptions, a phenomenon often termed "researcher degrees of freedom" or "p-hacking".

Because the binning process is heavily supervised, the quality of the output of these methods depends entirely on the validity of the assumptions made in the binning process. As such these methods leave much to be desired in terms of predictive power and reproducibility. Further, a great deal of variability in the dependent variable is lost in the process of binning even if the binning process is well-grounded in reality, such that the methods lose a large amount of statistical power even when employed correctly.

It would therefore be desirable for a new method for detecting GxEs to employ an unbinned, unsupervised approach to detection of GxEs that does not require researcher manipulation or transformation of the data prior to analysis.

OBJECTS OF THE INVENTION

Accordingly, an object of the present invention is to provide a mechanism for detecting GxEs which does not require binning of the dependent variable of interest, such that concerns over the assumptions underlying this binning do not undermine the method's results.

Another object of the present invention is to increase the statistical power for the detection of GxEs in order to produce results which are more predictive, more viable and more reproducible than traditional methods.

A third object of the present invention is to enable GxE detection for dependent variables for which binning is not useful (continuous variables), or for which valid binning thresholds are not able to be determined.

A fourth object of the present invention is to define a mechanism for evaluating multiple different positions in the genome that are relevant to a given GxE in the context of one another in order to increase the accuracy of predictions made based on these signals.

Still another object of the present invention is to allow efficient, economical, and practical apparatus and methods fulfilling the other objects of the invention.

Other objects, features, and advantages of the present invention will be appreciated when the present description and appended claims are read in conjunction with the drawing figures.

BRIEF DESCRIPTION OF THE DRAWING FIGURES

FIGS. 2B-C show how an example gene-environment interaction regulating response to smoking would not be observed as an increase in difference in an example phenotype, telomere length, as dizygotic monozygotic twins increase in age (FIG. 2B), while there would be an increase in difference telomere length with age in monozygotic twins (FIG. 2C).

FIG. 3A demonstrates how observations in twin datasets and the patterns which apply to monozygotic twins but not dizygotic twins would be observed as a table.

FIG. 3B demonstrates how observations in twin datasets and the patterns which apply to monozygotic twins but not dizygotic twins would be observed graphically.

Figure 4A:
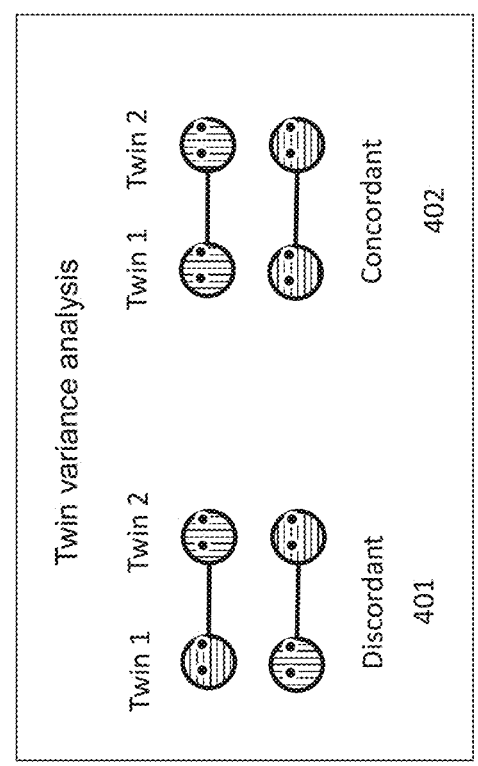

FIG. 4A shows how discordant and concordant comparisons are defined for this algorithm, with crosshatching indicating genotype.

Figure 4B:
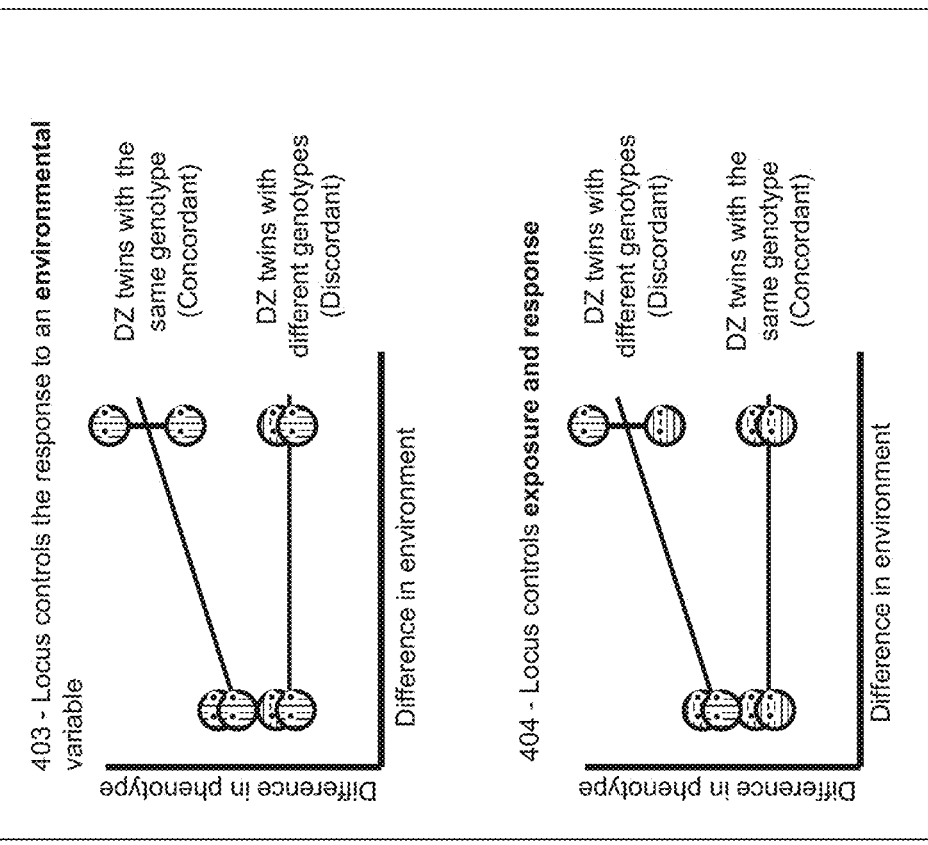

FIG. 4B illustrates a method of discovering loci that regulate GxEs in twin datasets graphically and demonstrates the logic utilized in the algorithm to identify gene-environment interactions.

Figure 5B:
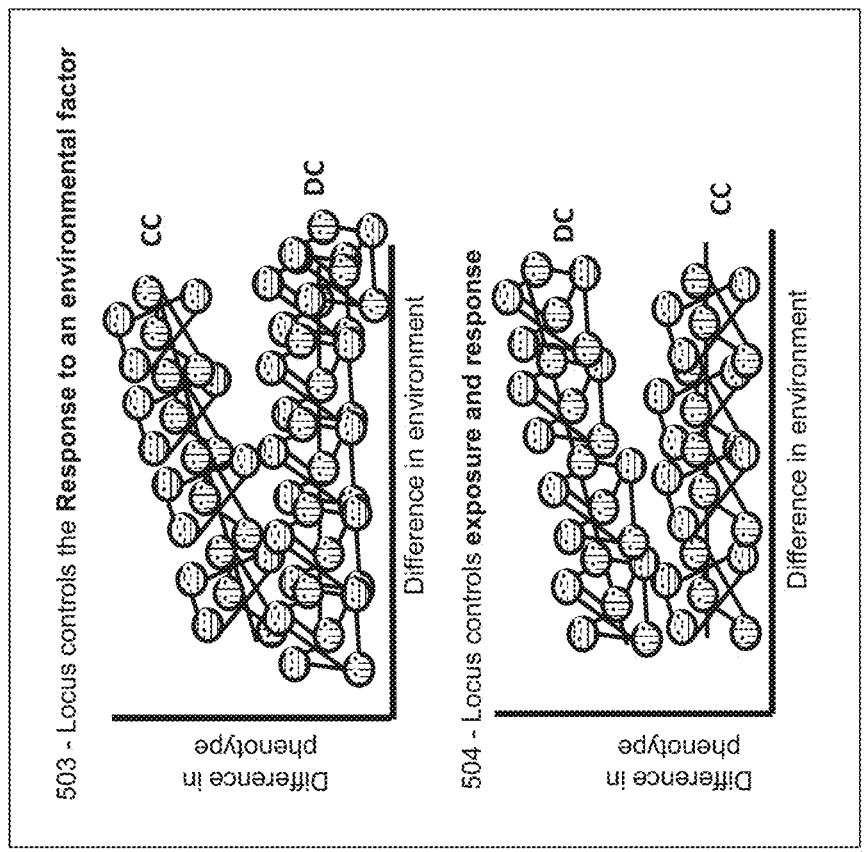
Figure 5A:
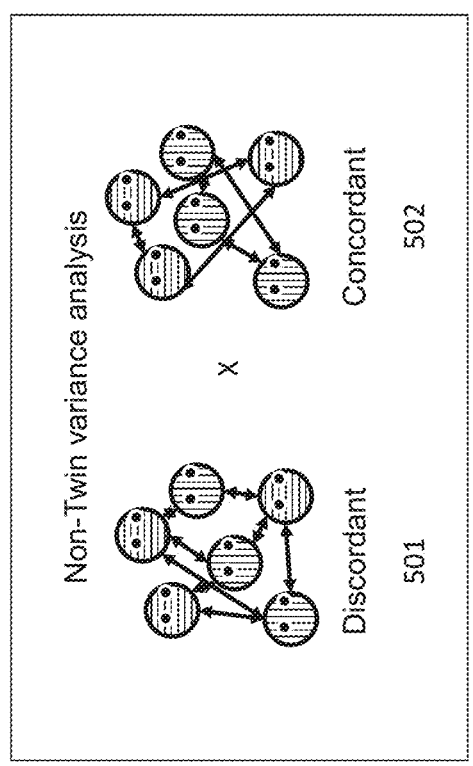

FIG. 5A graphically shows how discordant and concordant inter-individual comparisons are defined and illustrates logic for adapting the method of FIG. 4 to use non-twin datasets.

FIG. 5B graphically demonstrates the method the algorithm uses to identify gene-environment interactions and illustrates logic for adapting the method of FIG. 4 to use non-twin datasets.

Figure 6:
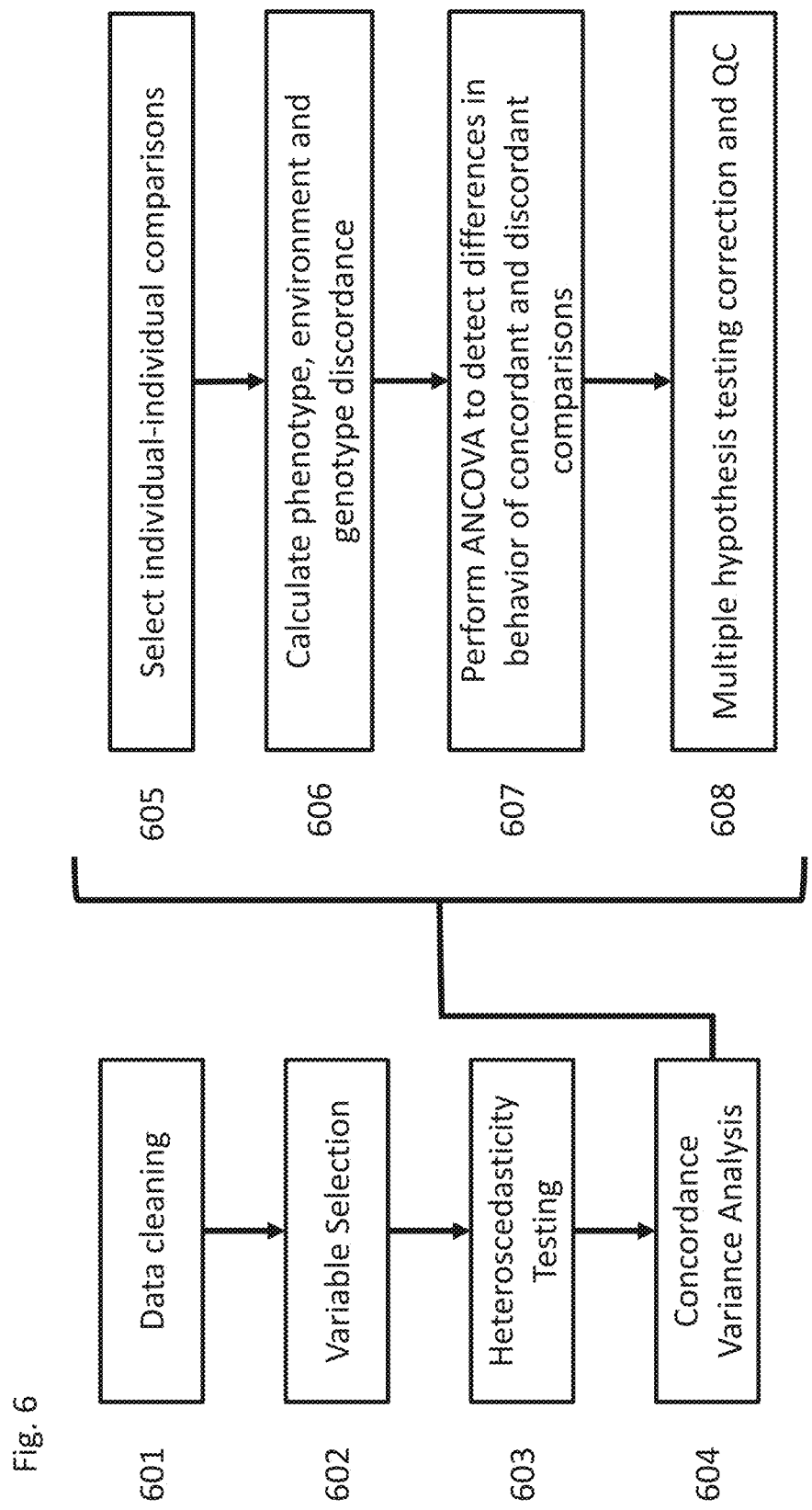

FIG. 6 shows an overview of the procedural steps used on a preferred embodiment of the invention to perform GxE detection FIG. 7 shows how genotypes at detected GxEs are used in a preferred embodiment to make a composite "genotype score" based on genotype at all loci detected with the method for comparison to a source population in a preferred embodiment.

Figure 8:
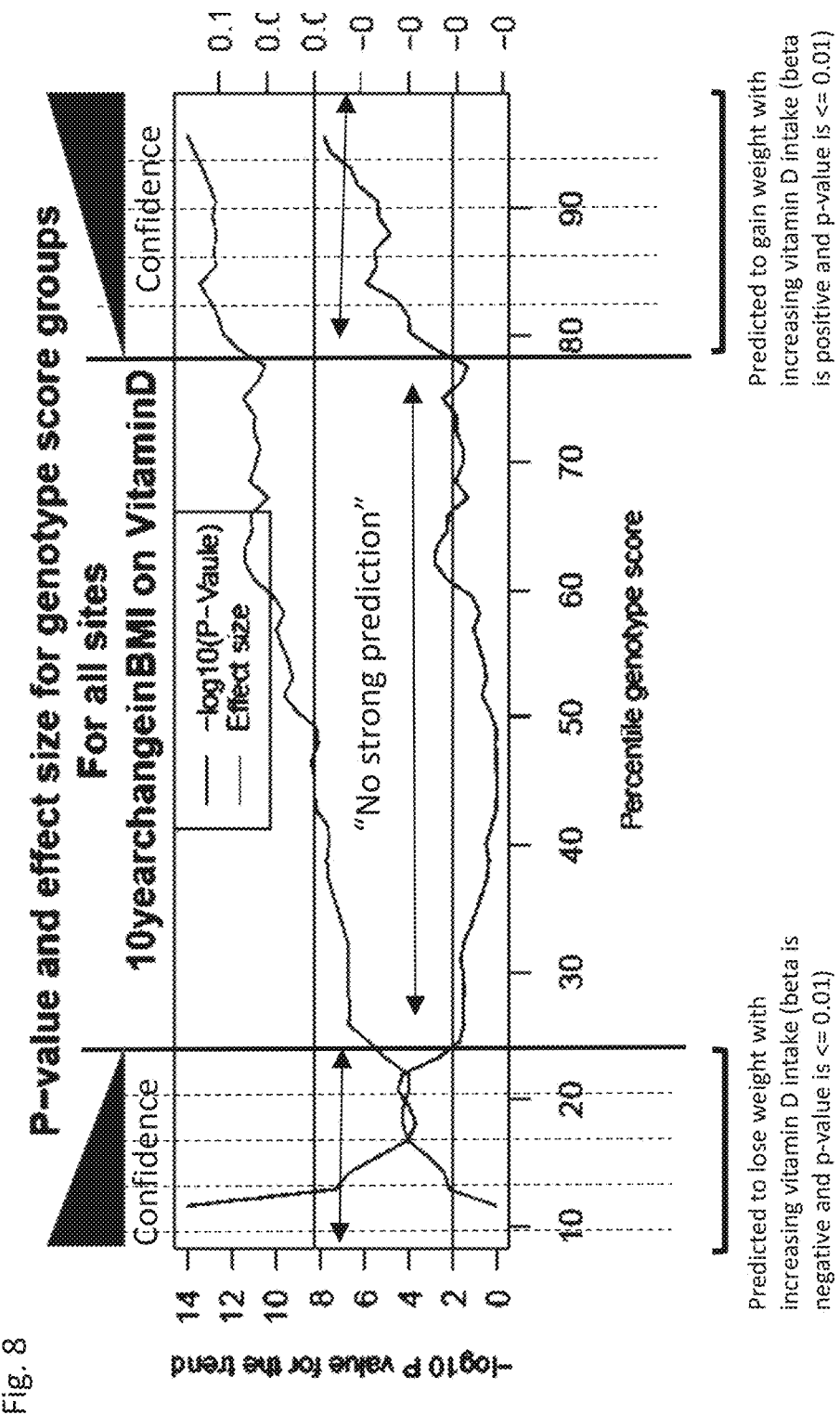

FIG. 8 shows how a genotype score is used in a preferred embodiment to make a prediction about individual responses in GxEs FIG. 9A shows an overview of a process utilized in a preferred embodiment for creating simulated genetic, health and environmental data to evaluate the method's ability to detect GxEs and make accurate predictions based on them.

FIG. 9B shows the parameters used in the simulation described in FIG. 10, FIG. 11A, FIG. 11B, FIG. 12A and FIG. 12B.

Figure 10:
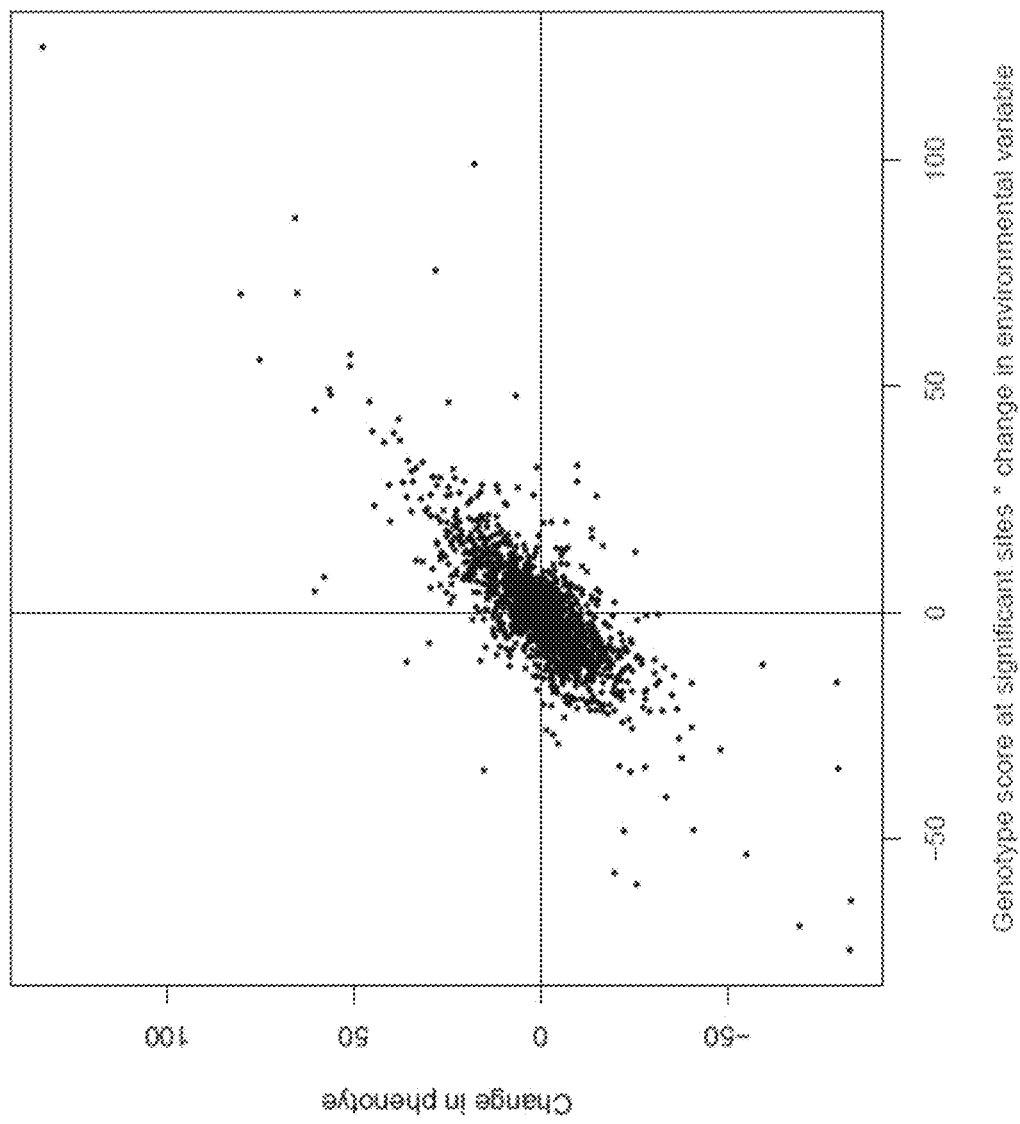

FIG. 10 shows an example of how predictions made by the method (x-axis) relate to the change in phenotype in a simulated intervention (y-axis), showing the accuracy of the predictions made by an embodiment of the method in this simulation.

Figure 11B:
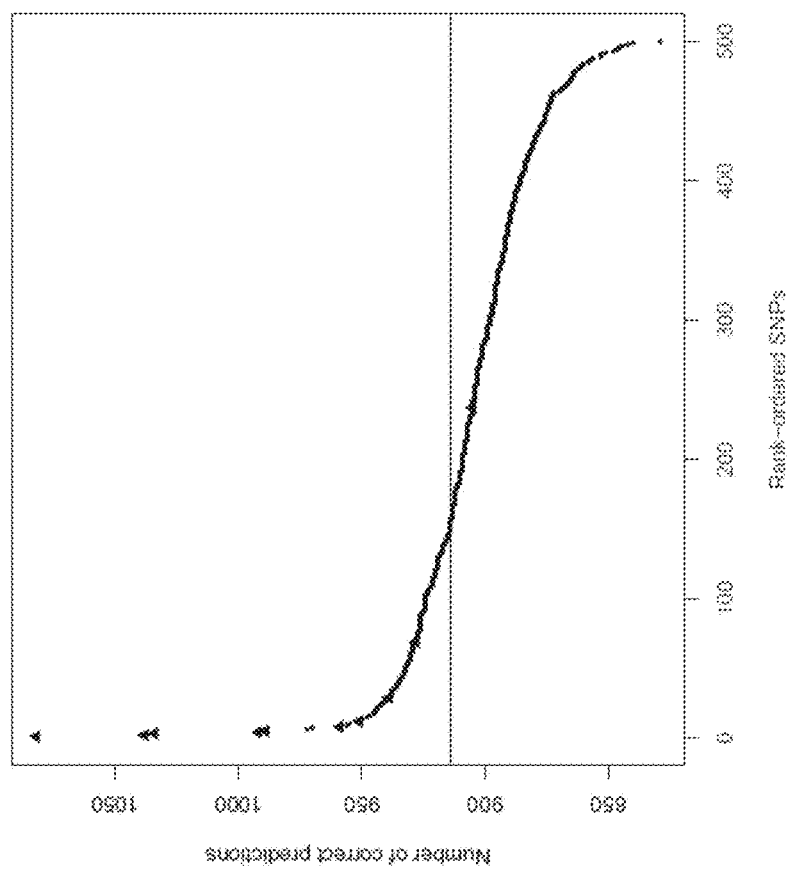
Figure 11A:
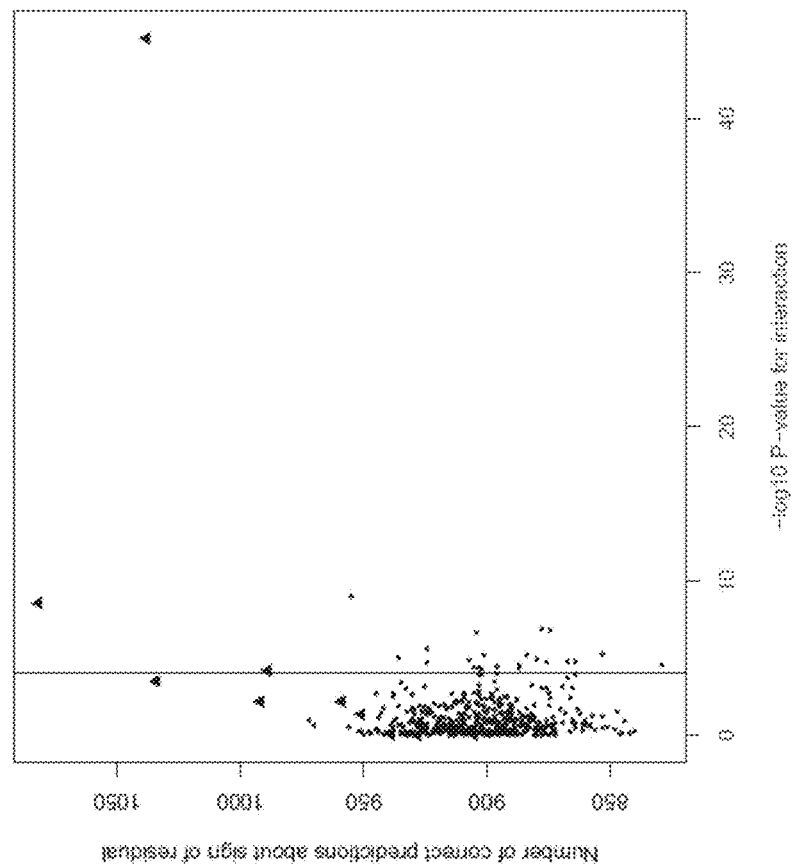

FIG. 11A shows the number of correct predictions made by each locus evaluated in an example simulation versus the p-value for non-homogeneous regression slopes in the simulation using parameters described in FIG. 9A and FIG. 9B.

FIG. 11B shows the number of correct predictions about the sign of the residual in a linear model with change in phenotype as the dependent variable and genotype score multiplied by change in environmental factor as the independent variable in a rank-ordered way from most frequently predictive to least frequently predictive; this allows quantification of how often a site's prediction is consistent with the population's deviation from expected behavior, a trait of causal loci, with the number of correct predictions expected by chance displayed as a horizontal line.

Figure 12B:
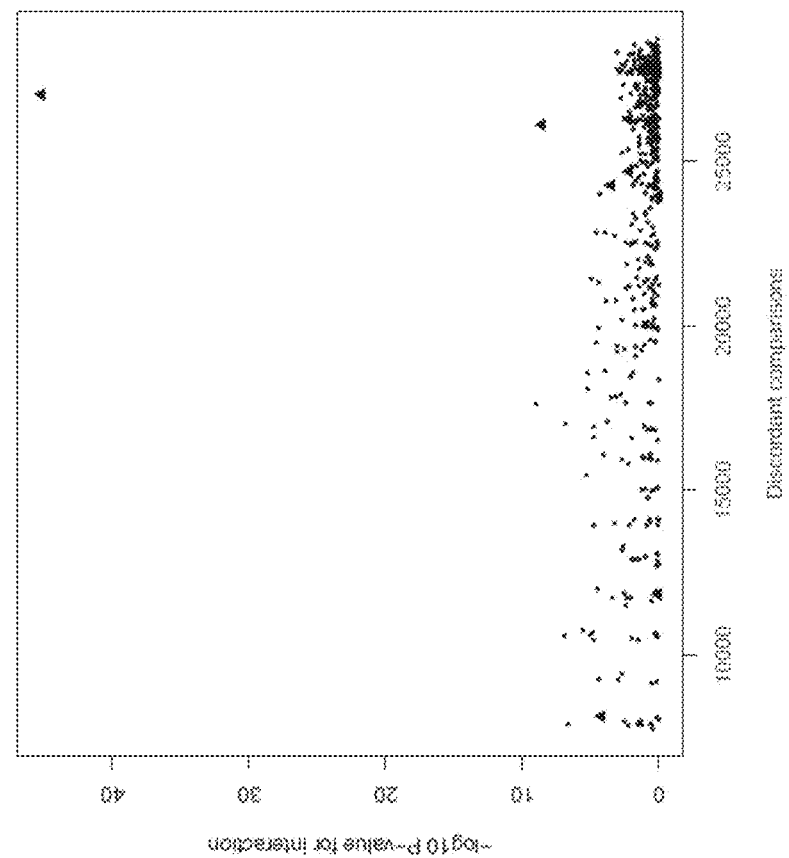
Figure 12A:
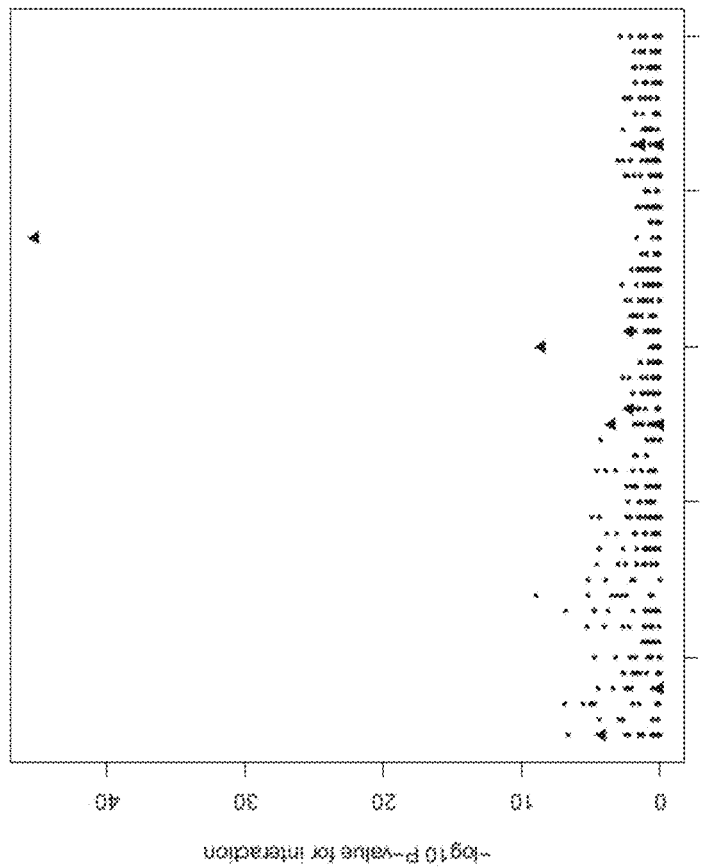

FIG. 12A shows the −log 10-transformed p-values for non-homogenous regression slopes for each locus versus minor allele frequency.

FIG. 12B shows the −log 10-transformed p-values for non-homogenous regression slopes versus the number of discordant comparisons made in the GxE detection step, with causal loci indicated by triangles and non-causal loci indicated by points.

BRIEF SUMMARY OF THE INVENTION

In accordance with these and other objects of the present invention, a brief summary of some exemplary embodiments is presented. Some simplifications and omissions may be made in the following summary, which is intended to highlight and introduce some aspects of the present invention, but not to limit its scope. Detailed descriptions of preferred exemplary embodiments adequate to allow those of ordinary skill in the art to make and use the inventive concepts are provided later.

The invention is preferentially used with datasets containing information about one or a plurality of dependent variables of interest and two or a larger plurality of independent variables of interest. The invention may be applied to any kind of dependent and independent variables.

The Invention is preferentially implemented using data storage means to store an input dataset and an output results set. Data storage means can be implemented as electronic or optical data storage means, which may be rotating disk drives, solid state disks, non-volatile memory, or other data storage means. Calculations on the data are preferentially performed by computing means consisting of one or a plurality of data processing units connected to or incorporating memory means and data input-output means. In some embodiments one such computer system is utilized, while other embodiments utilize a plurality of computer systems. In some embodiments one or a plurality of computer systems are directly connected to data storage means, while in other embodiments utilize one or a plurality of network connections to transfer data between data storage means and computing means. In a preferred embodiment, the algorithms and operations disclosed herein are implemented in software code utilizing one or a plurality of programs. In some embodiments the software code is implemented as firmware, while in other embodiments stored programs are utilized. In some embodiments the software code is written in the R computer language, while in other embodiments one or a plurality of other languages are utilized.

Some embodiments of the invention detect interactions between one or a plurality of past or present environmental variables and one or a plurality of genetic loci with respect to a one or a plurality of phenotypes of interest. Other embodiments detect interactions between one or a plurality of past or present environmental variables with respect to one or a plurality of other or overlapping past or present environmental variables. Still other embodiments detect interactions between one or a plurality of genetic loci and one or a plurality of other or overlapping genetic loci. Other embodiments utilize non-genetic biological information such as RNA expression, methylation, past or present microbiome data, past or present histone modification, past or present heritable or infectious medical conditions, past or present information about bodily functions, past or present antigen profiling of the immune system, past or present optical, x-ray, magnetic resonance, computed tomography or positron emission imaging data in addition to or in place of genetic information or environmental variables of interest, or other information. In the remainder of this document, dependent variables of interest will be referred to as "phenotypes" and independent variables of interest will be referred to as "environments", but this is not intended to limit the generality or applicability of the invention to these categories of variables or information.

A biological system, such as a population of humans, which contains a heterogenous response to one or a plurality of the phenotypes of interest which are influenced by genetics and one or a plurality of an environmental factors, is a biological system containing GxEs. Such GxEs can be detected by comparing the behavior of concordant individuals (individuals with the same genotype at a specific locus under evaluation) and discordant individuals (individuals with a different genotype at a specific locus under evaluation). In such a system individuals with the same genotype at one or a plurality of loci that control a GxE (for example, by in some way altering biological function based on different genotype at the said locus or loci) will become farther apart in terms of the phenotype affected by the GxE of interest (the absolute value of the difference in value of the phenotype will rise) as they become farther apart in terms of exposure to the environmental factor that is relevant to the GxE. The difference will increase because each individual's response to any particular value of the environmental stimulus is the same, but they are each experiencing different amounts of that stimulus, resulting in increasingly different values of the phenotype as the difference in environmental exposure becomes more pronounced. In contrast, in that same system, discordant individuals (individuals with different genotypes the locus or loci which control the GxE) will, on average, not diverge in the phenotype of interest as they diverge in the environmental factor of interest. They will not diverge because a change in the environmental factor is as likely to increase their difference as it is to decrease their difference. It is likely that in a large population a similar number of inter-individual comparisons will contain as many individuals converging in phenotype as are diverging in phenotype, resulting in no trend in the population as a whole.

Descriptive statistics therefore focus on the ability to reject the null hypothesis that concordant and discordant individuals at each evaluated genetic locus have the same response to the environmental factor of interest with respect to the phenotype of interest. Loci which strongly reject the null hypothesis are likely to harbor GxEs, and these GxEs can be used in follow-up analyses to make predictions about response to the phenotype of interest in the broader population.

In order to detect GxEs, some embodiments of the invention compare a plurality of individuals' genotypes and categorize them as having the same genotype at each locus of interest (concordant), or having a different genotype at the each such locus of interest (discordant) on a pair-by-pair and locus-by-locus basis. A preferred embodiment utilizes two linear models: the first linear model, the Discordant Difference Model (DDM), is a linear regression using only those inter-individual comparisons (dyads) where the individuals have a different genotype at each locus evaluated. The DDM uses the difference in phenotype between the individuals in each dyad as the dependent variable and the difference in environmental factor between the individuals in each dyad for discordant groups as the independent variable. The second linear model, the Concordant Difference Model (CDM), is a linear regression using only those dyad comparisons where the individuals have the same genotype at the locus evaluated. The CDM uses the difference in phenotype between the individuals in each dyad as the dependent variable and the difference in environmental factor between the individuals in each dyad as the independent variable. These models are created in order to test for non-homogeneous regression slopes between the DDM and CDM. The resulting signal, a difference in regression slopes between the DDM and CDM, is used in this embodiment to identify loci involved in one or a plurality of Gene-Environment-Interactions (GxEs).

A GxE causes individuals with the same genotype at the locus or loci controlling the GxE, and thus the same response to an environmental factor, to have progressively more different phenotype values as they have more different exposures to said environmental factor. In a preferred embodiment, GxEs are quantitatively detected at loci where the regression slopes between the DDM and CDM are not the same and the individuals in the CDM become increasingly different in phenotype value with increasing difference in environmental factor (the slope of the CDM is positive). Such increasing differences indicate that individuals with the same genotype had the same response to an increasingly different stimulus. Detected interactions are preferentially described with one or a plurality of descriptive statistics, which in a preferred embodiment includes: p-value for the test for non-homogeneous regression slopes; p-value for interaction between the independent variables; coefficients of regression for one or both independent variables. A preferred embodiment produces two outputs at this stage; the p-value for non-homogeneous regression slopes is the primary output, in addition to a positive beta for the CDM (which indicates that individuals with the same genotype become increasingly different in dependent variable as they become increasingly different in independent variable and therefore have the same response to an increasingly different stimulus) to describe a candidate GxE. This embodiment then uses a standard Bonferroni correction of the p-value for non-homogeneous regression slopes between the CDM and DDM to reduce the possibility of spurious results due to multiple hypothesis testing. Other embodiments may instead use non-linear models, machine learning algorithms, or other means that will be apparent to someone of average proficiency in the art, in place of the CDM and DDM in order to test for differences in behavior between concordant and discordant comparisons as a marker of underlying GxEs.

An example of an application of the preferred embodiment of the invention is described here for illustration. To detect loci that control a GxEs relating to self-reported joint pain frequency as the phenotype and self-reported smoking frequency as the environmental factor in a dataset of 5000 individuals which contains information about joint pain frequency, smoking frequency and genotype data on 500,000 single nucleotide polymorphisms, the following procedure could be utilized: Dyads are created by randomly selecting pairs of individuals from the population with replacement for a total number of dyads equal to 45,000 (a number of comparisons which was selected in this example via interpretation of a simulation described with reference to FIG. 9A). Other embodiments utilize different numbers of dyads. The absolute value of the difference in self-reported joint pain and smoking frequency is then be computed for each dyad, and each dyad is be evaluated to determine if it is concordant (has the same genotype) or discordant (has a different genotype) at each of the 500000 loci considered. For each locus, a preferred embodiment then creates a CDM and DDM in order to test for non-homogeneous regression slopes for the regression of absolute value of difference in joint pain frequency as the dependent variable and the absolute value of the difference in smoking frequency as the independent variable, at each locus considered, using the concordance data for that locus. Any dyad may be concordant for one locus such that both individuals have the same genotype at that locus and discordant at another locus such that they have different genotypes even though the individuals in the dyad did not change. The concordance of a dyad is evaluated on a locus-by-locus basis for each dyad. For example, a dyad may be concordant at one locus because they have the same genotypes, and discordant at another locus because they have different genotypes. The result of this process is a unique CDM and DDM for each locus. This CDM and DDM are then used to detect non-homogeneous regression slopes. Such a difference in regression slopes indicates the presence of a GxE.

When one or a plurality of GxEs have been detected by the preceding steps, a preferred embodiment employs a linear modeling-based approach to make predictions about response based on any given individual's genotype at all or a subset of the GxE loci detected in the previous step. This process creates a linear model with the phenotype as the dependent variable and the environmental factor as the independent variable for each possible genotype at all GxE loci detected in the previous step, and stores the beta ("strength value") and p-value for this linear model for later use. A "genotype score" is then constructed for each individual or a subset of individuals in the source population, which is the sum of the strength values for the genotype-specific linear model of the source population corresponding to that individual's genotype at each GxE locus. The source population is then sorted in ascending or descending order by genotype score, and linear models with the phenotype value as the dependent variable and the environmental factor as the independent variable are constructed for subsets of the sorted population. This results in "segments" of the population with a unique linear model of the way that the phenotype responds to the environment, which are identified by mean genotype score within each segment. The intent of this segmentation and linear modeling is to identify the individuals in the source population genetically closest to any given individual (the "test individual") based on genetic similarity at the loci considered, and to make a prediction about the test individual based on the response of the group of individuals in the source population that correspond most closely with the test individual in genotype at the GxE loci previously identified. A prediction is then made that the test individual will respond to the environmental factor in the same way as the segment of the population with a genotype score mean closest to the test individual's genotype score.

In a preferred embodiment, optimal parameters for use of the method for each given application are initially determined via a simulation that creates a population of simulated individuals that have phenotype, environment and genetic data with a variable number of causal GxEs and data that reflects these GxEs. The method can then be employed within this context with variable values for a number of parameters and the frequency of type I and type II error can be determined, and parameters that minimize errors in the context of this environment can be determined through a sensitivity analysis procedure that uses the method with different values for these parameters. In a preferred embodiment this procedure is used prior to the method in a source dataset in order to optimize the results.

The current invention can be applied to any arbitrary fraction of the genome including the whole genome, as well as one or a plurality of genetic insertions, deletions and rearrangements, and any other perturbation of sequence-level, transcriptional, epigenetic or functional change to the genome, cell, organism, population or species. The preferred embodiment employs a linear modeling-based approach to make predictions about loci where GxEs are detected, however the GxE detection method and the method by which predictions are made about GxE loci are distinct. Therefore, other embodiments of the invention can utilize one or a plurality of other interpretation methods, as an alternative to or in addition to those disclosed for the preferred embodiment. Such methods can include: polynomial regression, nonlinear regression, machine learning approaches or other approaches which will be apparent to a person of ordinary skill in the art. Such methods may be used to make predictions based on the loci identified with the methods described. Some embodiments evaluate higher-order interactions such as epistasis and haplotype effects or other interactions within the genome or between the genome and other aspects of the cell, organism, population or species. Other applications and uses of the invention will be apparent to a person of ordinary skill in the art.

General Description

The protocols to be described in detail later and the drawing figures make a number of simplifying assumptions for concreteness and for clarity in exposition. It will be appreciated, however, that these should not limit the scope of the invention.

The choice of party or entity names, and the number of entities are also examples of choices made for clarity and convenience. Naturally, the inventive concepts disclosed here should not be interpreted as limited to particular types of entities such as genetic loci, phenotypes, environmental factors, and GxEs. They are applicable in any context where one variable may be altered by the interaction of two other variables, or where there is interdependency in any system containing at least three variables.

There may also be additional entities and entity types in some embodiments.

DETAILED DESCRIPTION OF PREFERRED EMBODIMENTS

The described system and method allows discovery of Gene-Environment Interactions (GxEs) without the requirement to reduce phenotypes of interest to case/control status, which improves statistical power and removes a common source of user error. The binning required to perform case/control logic-dependent analyses throws away substantial information. For example, a dataset that includes BMI data about thousands of people stores that as a continuous variable with a distribution generally between 18 and –40; to use case/control logic one must reduce this distribution to a binary (obese or not obese) distribution, which dramatically reduces the information content of the data. The method does not require binning which is why this method has greater statistical power than previous methods.

The system and method uses, which is more useful for biological applications than the two variable analysis exemplified by Genome-Wide Association Studies (GWAS) and other modes of prior art because all results of three variable analysis naturally lend themselves to the format, "If X and Y, then Z". For example, if the user has the genotype AA at a given site and they increase their intake of caffeine, then we would expect a decrease in BMI. Two variable analyses are most useful in the format of: If X, then Y. For example, if the user has AA at a given site then they are more likely to be overweight (BMT>25). Existing methods to detect GxEs utilize case/control logic to use a two-variable method where a three-variable method would be best. In the above example, conventional GWAS could be used to identify sites that govern the BM1:caffeine phenotype:environment pair by conducting a study where individuals were asked to increase their caffeine intake and monitoring their BMI; individuals with a decrease in BMI over a certain user-defined value with increased caffeine intake would be treated as "cases" and those that did not would be "controls", and a conventional GWAS would be used to identify sites with an unexpected allele frequency in the cases compared with the controls; note that the definition of what a "case" is, and the change in BMI required to be considered one, would have a dramatic impact on the results. This method allows productive, application-driven use of studies with a single measurement of a population without an intervention, as well as removes the requirement for a definition for case or a control.

The described invention uses inter-individual comparisons (dyads) to simplify the three-variable analysis. This allows the use of well-established statistical tests like Analysis of Covariance (ANCOVA) in new ways, which reduces the amount of mathematical innovation required. The invention examines trends in the distance between individuals in the population as a function of the concordance status at each site on the genome evaluated. For example, to identify pieces of the genome that regulate the relationship between BMI and caffeine, the invention compares a number of individuals within the population (generally >50,000 dyads). It computes, for each dyad, the absolute value of the difference in their BMI and the absolute value of the difference in their caffeine intake. For each position in the genome we have information about, it then computes, for each dyad, if they have the same genotype at that position or a different genotype at that position. It then uses ANCOVA to determine if the slope of the linear regression of the difference in BMI on difference in caffeine intake, the CDM is different in the concordant group, the group of dyads with the same genotype, than the discordant group, the dyads with a different genotype, the DDM. It does this for each locus, and the marker for a detected signal is the p-value for a difference in slopes from ANCOVA. Loci with significantly different slopes between the CDM and the DDM and a positive slope in the CDM are considered hits, because individuals with the same genotype have progressively more different phenotype values as they have more different exposures to the environment—this suggests that the locus evaluated in some way controls this relationship. because individuals with the same genotype at that site behave as if they have the same response to the environmental stimulus.

The invention utilizes the insight that if two individuals have the same response in terms of a phenotype to an environmental factor, those individuals will become progressively farther apart in phenotype as they become farther apart in exposure to the environmental factor to detect pieces of the genome relevant to each phenotype:environment pair. Looking for this signal, rather than simple differences in phenotype or biases in allele frequency among cases and controls as most existing GxE methods do, allows for greater power and the ability to discover signals other methods miss.

The invention does not rely on case/control logic, which allows examination of truly continuous phenotypes. For example, existing methods would require a data scientist to define "obese", in terms of a cutoff value required to be classified as a "case" or "affected" for obesity to look for GxEs related to obesity, whereas this invention can use BMI directly without imposing a definition of obese. This is important because where the data scientist draws the line— what they define as obese in this case—will influence the results; different definitions of the phenotype may yield dramatically different results. The described invention is not limited in that way, and can the raw data without any unnecessary processing. This removes a common source of artifactual results.

Existing methods identify sites with case/control logic and evaluate those sites in isolation, whereas this invention evaluates all sites detected as a whole, constructing predictions for a given sample based on how the individuals in the source dataset closest to that sample at the sites relevant to a given Phenotype: Environment pair responded. This allows predictions for an individual to be calculated taking into account their entire genome, rather than each site individually with no information related to how it interacts with the other aspects of a subject genome.

The invention includes a simulation framework, that creates a simulated population which includes a number of GxEs. Because it's a simulation, it can be used as a test-bed framework to both prove that the invention works (FIGS. 9, 10, 11 and 12), but also to quantify error rates given the parameters in a given source population, which is useful for empirical optimization of analysis parameters when using the invention on a new source dataset.

The invention can be used to detect environment-environment interactions, time dependent trends and a wide variety of other signals by modifying one or more axes of the three-variable analysis.

Figure 1:
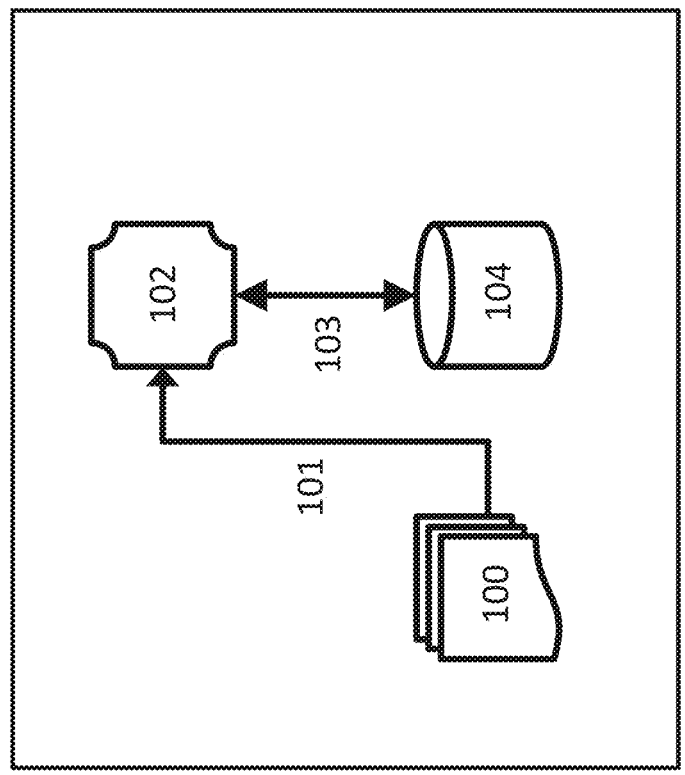
FIG. 1 shows a schematic diagram of components of the system

FIG. 1 depicts a schematic of components in the system. One or a plurality of Datasets 100, preferentially containing genomic data, environmental data and phenotypic data in a digital form, is entered into a data storage means 104 via a data entry means 101 connected to data processing means 102, which is connected to the data storage means 104. The data entry means 101 may be a direct connection such as a USB port, a wireless connection such as WiFi, a hardwired connection such as ethernet, or any other connection. The data entry means 101 preferentially is connected to a data processing means 102, which processes the Dataset 100 and stores it on a data storage means 104 via a data connection 103. The data processing means 102 preferentially contains one or a plurality of central processing units, a random access memory, and input-output means. The data processing means 102 can then analyze the Dataset 100 and store a results set on the data storage means 104. Although FIG. 1 depicts only one Dataset 100, one data entry means 101, one data processing means 102, one data connection 103 and one data storage means 104, some embodiments utilize a plurality of one or a plurality of these components and one or a plurality of variations of these components. The following figures and descriptions refer to the operations performed by the data processing means 102 under control of one or a plurality of software programs. In a preferred embodiment, the algorithms and operations disclosed herein are implemented in software code utilizing one or a plurality of programs. In some embodiments the software code is implemented as firmware, while in other embodiments stored programs are utilized. In some embodiments the software code is written in the R computer language, while in other embodiments one or a plurality of other languages are utilized.

Figure 2A:
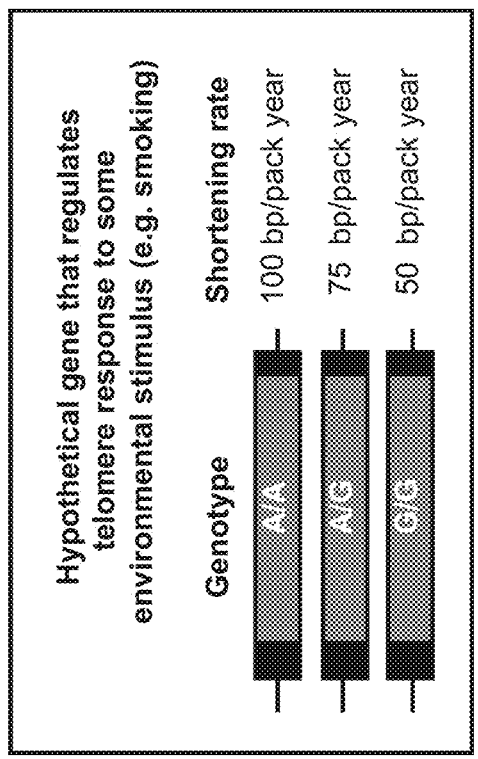
FIG. 2A shows an example gene-environment interaction wherein genotype at a site controls the rate of telomere shortening in response to smoking.

FIG. 2A shows a hypothetical case of a single nucleotide polymorphism that controls the response of some phenotype, in this case telomere length, to some environmental stimulus, in this case smoking. In this hypothetical scenario, individuals with the A/A genotype shorten at 100 base pairs (bp) per year, whereas individuals with A/G or G/G genotype shorten at 75 bp and 50 bp per year respectively. In this example A/A individuals are sensitive to the environmental factor and G/G individuals are resistant. This hypothetical scenario would lead to the pattern observed in FIG. 2B and FIG. 2C, FIG. 2B and FIG. 2C each diagram the absolute value of the difference in telomere length between each twin in a twin-pair (Inter-Twin Variance in TL) versus age: FIG. 2B in Dizygotic twin-pairs and FIG. 2C in Monozygotic twin-pairs. As the population in this hypothetical scenario ages, the difference in exposure to the environmental factor (smoking) becomes increasingly different in each twin-pair, resulting in increasingly different telomere lengths in monozygotic twins. However, because there is mixture of different possibilities regarding which twin in each twin pair is more exposed to the environmental factor, which twin in each twin pair is more sensitive, and which twin has initially longer telomeres in each dizygotic twin-pair, these pairs are as likely to become more similar with respect to the phenotype as they are to diverge, resulting in no population-level trend.

FIG. 3A shows a table illustrating the possible combinations of: which twin in a twin-pair is more sensitive to an environmental factor; which twin is more exposed to the environmental factor, and which twin starts with shorter telomeres. These possibilities are graphically shown in FIG. 3B. All four possibilities for dizygotic twins: sensitive twin greater exposure diverging possibility 310, sensitive twin greater exposure converging possibility 311, resistant twin greater exposure diverging possibility 313 and resistant twin greater exposure converging possibility 314, lead to no net trend in the population as long as the twin-pairs are evenly distributed between the possibilities. Sensitive twin greater exposure diverging possibility 310 and resistant twin greater exposure diverging possibility 313 lead to increasing differences over time, however sensitive twin greater exposure converging possibility 311 and resistant twin greater exposure converging possibility 314 lead to decreasing differences over time. In a population evenly balanced between each of these scenarios, t\no population-level trend will be observed, since the twin-pairs are as likely to become more similar with respect to the phenotype as they are to diverge. Monozygotic twins are considered in initially longer telomeres twin smokes more monozygotic diverging possibility 312 and initially shorter telomeres twin smokes more monozygotic diverging possibility 315. Although monozygotic twins typically have similar telomere length at birth, at the time this hypothetical study begins, each member of the pairs of twins have been exposed to different environmental conditions and therefore they have different telomere lengths. Both initially longer telomeres twin smokes more monozygotic diverging possibility 312 and initially shorter telomeres twin smokes more monozygotic diverging possibility 315 lead to increasing differences in telomere length, which is visible as a population-level trend. The observations of FIG. 3A and FIG. 3B are only applicable to monozygotic and dizygotic twins, and do not apply to other individuals.

The models of FIG. 4A and FIG. 4B depict a method which is utilized in some embodiments for detecting genetic loci involved with GxEs using dizygotic twin datasets. FIG. 4A depicts a first step in the method, subsetting the population of twin-pairs into two subsets: a subset of twin pairs that have a different genotype (discordant) at each individual locus 401, and a subset of twin-pairs that have the same genotype (concordant) at each individual locus 402. A second step of the method is depicted in FIG. 4B: test for increasingly different phenotype values with increasingly different environmental factor values in concordant twin-pairs—essentially looking for "monozygotic-like" behavior in dizygotic twins with the same genotype at each locus. In some embodiments this is quantified by using a linear model utilizing a) difference in phenotype as the dependent variable and b) difference in environmental factor value as the independent variable. Such a model is utilized in these embodiments by looking for a statistically significant signal indicating that the regression slope in the model when applied to concordant twin-pairs is non-homogeneous with the regression slope of the same linear model applied to discordant twin-pairs. In such a case when the slope of the concordant comparisons is positive as is the case in Concordant Comparisons Diverging Model 403, this indicates the presence of a GxE. When the regression slopes between concordant and discordant comparisons are non-homogeneous and the discordant comparisons have a positive slope, this indicates the presence of a signal that controls the intrinsic rate of change in the phenotype as shown in Discordant Comparisons Diverging Model 404. This methodology has utility in detecting GxEs, and is an improvement over methods which utilize only monozygotic twins as study subjects, because Datasets 100 with data regarding dizygotic twins can be utilized A preferred embodiment of the invention implements a methodology which allows the use of one or a plurality of Datasets 100 with data pertaining to unrelated individuals. Because the occurrence of twins in the population is typically under 1%, a methodology which is capable of discovering GxEs utilizing data from unrelated individuals is a desirable and important capability. A preferred embodiment creates virtual twin-pairs (dyads) in a Dataset 100 of unrelated individuals by comparing a plurality of pairs of individuals that are randomly selected with replacement from the source population for each locus in the genome that is evaluated, and subsetting them into two sets of dyads: a first set of dyads 501 chosen such that the two individuals within each dyad have a different genotype at the locus of interest (discordant), and a second set of dyads 502 chosen such that the two individuals within each dyad have the same genotype at the locus of interest (concordant). Similarly to the method previously disclosed in reference to FIGS. 4A and 4B, loci with behavior as shown in CDM Diverging Model 503 exhibit increasingly different phenotype values as they exhibit increasingly different values of the environmental factor are candidate GxEs, indicating that the individuals in the dyad have the same response to an increasingly different stimulus. When the regression slopes between the CDM and DDM are non-homogeneous and the DDM has a positive slope, this indicates the presence of a signal that controls the intrinsic rate of change in the phenotype as shown in DDM Diverging Model 504.

A procedure used in a preferred embodiment to perform this analysis is depicted in FIG. 6, which schematically depicts some of the steps that can be performed in preparing the data for the analysis and selecting phenotype-environment pairs likely to harbor GxEs. At step 601 Data Cleaning, the source Dataset 100 is prepared for analysis. Such preparation may include range validations, elimination of data rows with invalid data (NAs or numerically-encoded answers which are not continuous), or other preparation. In a preferred embodiment, the source Dataset 100 is then formatted such that increasingly different numerical values indicate increasingly different phenotype or environmental values (i.e. the data is formatted in a continuous way); though it is not necessary for the data to be linear, the statistical evaluation to be performed later in this embodiment assumes a linear relationship between the numerical encoding of the data and the phenotype which was measured. As a further part of step 601, this embodiment performs data validation such that individuals for which data is incomplete are not included in the analysis. At step 602 Variable Selection, a set of phenotypic variables and a set of environmental variables are selected from Dataset 100 for analysis. Some Datasets 100 contain very large numbers of possible phenotype-environment pairs which would require extensive computational time and resources to process fully. Phenotype-environment pairs which exhibit heteroscedasticity are more likely to be affected by GxEs because one possible cause of bivariate heteroscedasticity is that the population contains individuals with different responses in terms of the phenotype to the environment; as such, individuals who are more exposed to the environmental factor are likely to be farther away from one another than less exposed individuals. Accordingly, at step 603 Heteroscedasticity Testing, a preferred embodiment uses the Breusch-Pagan test for heteroscedasticity for each phenotype-environment pair. Many other methods exist to detect heteroscedasticity, and other embodiments which utilize this step 603 use other such methods for heteroscedasticity testing. Still other embodiments test all phenotype-environment pairs or select pairs to be tested by other criteria or by other means. Step 603 results in a set of phenotype-environment pairs which may be more likely to yield useful predictions. In a preferred embodiment one or a plurality of such phenotype-environment pairs are analyzed via Concordance Variance Analysis 604 which, in this embodiment, is comprised of steps 605 through 608.

At step 605 select individual-individual comparisons (dyad), a plurality of dyads are created by randomly selecting pairs of individuals in the population to compare at each locus of interest. Work with the method has found that 45,000 comparisons is a good starting point for many phenotype-environment pairs evaluating health values and dietary information, however simulation and pilot work are preferentially performed for each application to determine a valid number of comparisons for each use; the method can generate artificially inflated significance at loci with small numbers of discordant comparisons and low minor allele frequency (discussed in greater detail in the descriptions of FIGS. 12A and 12B). In a preferred embodiment, the number of comparisons is set by running one or a plurality of simulations with parameters as close to the use-case of interest as possible, for any such parameters that are known (such as distribution of phenotype values in the population), and a reasonable estimate of parameters that are unknown (such as number of causal GxEs) with varying numbers of comparisons. An optimal number of comparisons to use is then empirically derived by evaluating the number of comparisons that most often correctly identifies causal loci. Other embodiments may use other means to determine the number of comparisons, such as high-dimensional interrogation of the parameter space of the simulation, a single constant number of comparisons for all purposes, a variable number of comparisons related to the sample size of the source population, or a number of comparisons derived from source, empirical, simulated data via machine learning algorithms or other means. At step 606, Calculate phenotype, environment and genotype discordance, the difference in phenotype value, difference in environmental value, and genotype concordance or discordance (if the individuals have the same genotype or a different genotype) for each locus to be evaluated is calculated for each pair of individuals. Next, at step 607 Detect differences in behavior of concordant and discordant comparisons, a detection process is performed to detect and quantify differences between the concordant and discordant dyads. In this embodiment this is implemented by creating two linear models: the first linear model, the Discordant Difference Model (DDM), is a linear regression using only those dyads where the individuals have a different genotype at each locus evaluated. The DDM uses the difference in phenotype between the individuals in each dyad as the dependent variable and the difference in environmental factor between the individuals in each dyad for discordant groups as the independent variable. The second linear model, the Concordant Difference Model (CDM), is a linear regression using only those dyads where the individuals have the same genotype at the locus evaluated. The CDM uses the difference in phenotype between the individuals in each dyad as the dependent variable and the difference in environmental factor between the individuals in each dyad as the independent variable. Linear regressions of the phenotype on the environmental factor for both concordant and discordant populations are also performed to evaluate the beta of any detected difference in regression slopes. The method's primary outputs for each locus of interest are the p-value for the test for non-homogeneous regression slopes between the CDM and DDM and the beta for the linear regression of difference in phenotype value on difference in environmental factor for the CDM. A locus considered as a candidate GxE if the p-value for non-homogeneous regression slopes between the CDM and DDM indicates that concordant and discordant comparisons have a different slope in a highly significant manner and the beta for the CDM indicates that concordant comparisons have increasingly different phenotype values as they have increasingly different environmental factor values (the beta is positive). In a preferred embodiment, a Bonferroni cutoff is used to determine the threshold of significance ($p<=0.05$/number of loci evaluated), in other embodiments other methods utilized, such as the Benjamini-Hochberg correction/cutoff, arbitrary significance thresholds (such as $p<=0.05$, or $p<=0.01$), thresholds defined empirically based on previous results in the source Dataset 100 or other datasets, thresholds set by machine learning algorithms or other methods. At step 608 Multiple hypothesis testing correction and QC, the output of the analysis is evaluated to account for the odds of observing each candidate GxE based on the number of loci evaluated, and a number of the candidate GxEs are then preferentially evaluated based on biological plausibility or other supervised or unsupervised criteria such as machine learning algorithms or direct visualization of the GxEs detected in order to do quality control. A preferred embodiment of the method uses a Bonferroni cutoff, $p<=(0.05/\text{number of loci evaluated})$ as a threshold for significance of non-homogeneous regression slopes.

The detection method described in FIG. 6 identifies positions in the genome likely to harbor gene-environment interactions, but does not address how to interpret these GxEs or use them to predict response in any given population. In order to accomplish this prediction. some embodiments utilize nonlinear models, machine learning algorithms, or other means that will be apparent to someone of average proficiency in the art. A preferred embodiment utilizes the methodology disclosed in FIG. 7.

FIG. 7 depicts, in schematic form, some of the steps used in a preferred embodiment of the invention to create predictions regarding GxEs about individuals not present in the source population. In this embodiment, a linear modeling approach based on the principle of prediction by comparison to the source population is utilized. Other embodiments may use other methods such as machine learning, nonlinear or polynomial regression, or other methods. At step 701 Extract genotype for entire source population at detected sites, in a preferred embodiment, genotypes for the source population at the sites of interest are extracted for loci that are considered GxEs, as a result of the steps previously disclosed. This step is performed in a preferred embodiment to reduce memory requirements and as such is optional based on the size of the Dataset 100 and the memory capacity of the data processing means 102. Next, at step 702 Linear modeling of depVar indVar for each possible genotype at all sites of interest, in a preferred embodiment a linear regression is conducted of the phenotype value (depVar) on environmental factor (indVar) for each possible genotype at each locus of interest. Other embodiments may use other methods such as machine learning, nonlinear or polynomial regression, or other methods to interpret each locus of interest. At step 703 Use genotype-specific betas to compute total "genotype score" for each individual in source Dataset 100, in a preferred embodiment the betas for the linear models relating to each individual are grouped, and a score (the "genotype score") is calculated. In some embodiments this calculation is performed by adding the betas for the individual's genotype at each locus from the linear models, stored in a "strength file", while other embodiments may utilize approaches that consider loci in the context of other loci or use non-linear models, polynomial models or machine learning algorithms. At step 703 Sort source population by genotype score and construct moving linear models of depVar-indVar for different ranges of genotype score, in order to make a prediction about individuals not present in the source population, this embodiment of the method uses a prediction by comparison technique, because a genotype score can be calculated for individuals not present in the source population based on genotype alone, and a prediction can be made about their response to the environment in terms of the phenotype by determining the relationship between phenotype and environment in individuals in the source Dataset 100 with a similar genotype score. This is accomplished in this embodiment by sorting the source Dataset 100 in ascending order by genotype score, and constructing a linear model for an arbitrary number of segments of the population segmented by genotype score. For example, a source Dataset 100 with data on 6000 individuals can be broken up into ten segments of 600 individuals each, with a first segment composed of the 600 individuals with the lowest genotype scores, a second segment composed of the individuals with the 51st through 651st lowest genotype scores, a third segment composed of the 101st through 701st lowest genotype scores, continuing in this manner for the entire source Dataset 100. At step 705 Make predictions about response based on response of nearest section of moving linear models, a linear regression of the phenotype on the environment in each segment of the source population in the Dataset 100 is performed. This regression yields a p-value for the regression and a beta value indicating the direction and magnitude of the response for each segment, which is used in this embodiment to make a prediction about one or a plurality of individuals not present in the Dataset 100, based on their genotype score and these values in the source population segment in the Dataset 100 closest to their genotype score.

FIG. 8 depicts a graph of the betas and p-values of the linear regression of the embodiment described above, with reference to FIG. 7. Interpretation and application of the betas and p-values for the linear regressions of the segmented source population depends on the intended use of the results; a preferred embodiment uses a p-value threshold <=0.01 for significance, and the beta value of the regression to predict magnitude and direction of the response. FIG. 8 shows a graphical representation of the output of the moving linear modeling process, with −log 10-transformed p-value on the left y-axis and beta for the regression models of change in BMI over 10 years and vitamin D intake in one source population evaluated on the right y-axis, with the percentile value for genotype score on the x-axis; each point on both lines is a given segment of the source population, with the segments with the lowest genotype scores on the left and segments with the highest genotype scores on the right. Other embodiments may use other techniques to make interpret and make predictions about response based on the GxE loci identified in previous steps, such as machine learning algorithms, nonlinear or polynomial regression, models incorporation the interaction between different genetic or environmental factors or other techniques familiar to practitioners of ordinary skill in the art.

FIG. 9A is a schematic depiction of steps utilized in a preferred embodiment In order to define the parameters used in a preferred embodiment of the previously disclosed methodology for discovering GxEs, and to estimate the rates of type I and type II error in the method in the context of data that is representative of the data to be used in the method. The purpose of using representative simulated data is to verify how often and under what parameters the method makes correct predictions in the context of data where certainty about the correctness of the results is possible. The simulation method described in FIG. 9A allows a practitioner of the method to investigate how changes in the underlying rates of causal loci, and the extent to which the response to the independent variable of interest is controlled by GxEs modifies the output of the method, and to decide on parameters to use in the method, such as cutoffs for statistical significance, number of individual-individual comparisons to use for each locus evaluated, and minimum number of discordant individual-individual comparisons required to consider a given signal a GxE.

At step 900 Establish Simulation Parameters, parameters for the simulation are preferentially derived based on the distribution of values of dependent and independent variables of interest in the source Dataset 100 to be used in the method. For example, if the method were to be used on a source Dataset 100 with information about 1000 individuals' coffee intake (independent variable, mean intake of 1.5 servings/day and standard deviation of 0.75 servings/day) and body-mass index (BMI, dependent variable, mean of 25 and standard deviation of 3). the mean and standard deviation of the independent and dependent variables in the simulation would, in this embodiment, be set equal to the mean and standard deviation of the respective distributions in the source data. In the above example, for the simulation the mean of the independent variable would be set to 1.5 and the standard deviation would be set to 0.75, and the mean of the dependent variable would be set to 25 and the standard deviation would be set to 3. Values for the other parameters in the simulation would be set as near as possible to the values present in the source Dataset 100, for example in the above dataset the sample size for the simulation would be set to 1000.

At step 901 Generate simulated genotype data, a simulated environment is constructed utilizing the parameters identified in step 900. A number of GxEs in simulated genetic data are created utilizing parameters identified in step 900. The number of GxEs created are preferentially based on an estimate of the number of GxEs present in the source data. A noise distribution is added to the data to represent the number and extent of confounding factors present in the source data based on estimates about the fraction of the variability of the phenotype of interest which is due to GxEs and an estimate of the fraction of the variability of the phenotype of interest which is due to confounding noise or non-genetic factors.

At step 902 Create linkage between simulated sites, a correlation between genotype at one locus and genotype at another locus is created between the simulated loci. This linkage is included to simulate a number of confounding factors present in real genotype data resulting from the physical proximity of loci on chromosomes as well as biases that can result from ethnic stratification in real populations. Next, at step 903 Generate simulated GxEs, phenotype and environment values are generated for the simulated population and a proportion of the genetic loci are flagged as GxE-controlling loci and are assigned beta values indicating their change in phenotype relative to change in environment. This proportion is determined based on any information available about the extent of genetic control of the phenotype-environment pair, such as information obtained from twin studies, wet-lab experiments and previous iterations of this analysis. Next, at step 904 Simulate population based on noise parameters and GxEs, the simulated population's phenotype values are adjusted based on their genotype at each GxE locus in order to generate the signal that the method will be detecting and an adjustable amount of noise is added. Next, at step 905 Use Concordance Variance Analysis to Detect GxEs the GxE detection method previously disclosed is used in the same manner it is used with Datasets 100 containing real data to detect candidate GxEs. Next, at step 906 Simulate intervention based on detected GxEs, a change in exposure to the environmental factor is simulated and the population's new phenotype values after this change is calculated based on a tunable amount of noise and their genotype at the GxE loci. Lastly, at step 907 Compute error rates and evaluate output parameters, the method's error rates, correct prediction rates and the relationship between the method's predictions and the population's actual response is evaluated. This evaluation, and what values to use as cutoff values and indicators of statistical significance are based on the intended use of the results; a use of the method that does not entail much physical risk in the case of type T or type TI errors, such as predicting the response to a food may use a less stringent cutoff for statistical significance such as an arbitrary threshold, while more riskier environmental factors such as drugs and more important phenotypes such as cardiac function may use more stringent parameters. The parameters used in this embodiment and example of the simulation are displayed in FIG. 9B.

FIG. 10 depicts an example graph utilizing simulated data, produced at step 907 in the simulation example of FIG. 9A and FIG. 9B. The graph shows the change in the phenotype value following the simulated intervention on the y-axis, and the genotype score of the individual based only on the loci considered statistically significant by the GxE detection method multiplied by the change in the environmental variable in the simulated intervention on the x-axis. As such, individuals with a change in phenotype the same direction as that predicted by their genotype scorn and their change in environmental factor, correct predictions, are present in quadrant I and quadrant HI (top right and bottom left), while incorrect predictions are in quadrants II and IV. This output can be used to determine the type I and type II error rates of the predictions made about an individual under the parameters specified, in order to optimize the methods for each use-case.

FIG. 11A depicts an example graph utilizing simulated data, produced at step 907 in the simulation example of FIG. 9A and FIG. 9B. This graph evaluates how often each locus made a correct prediction about each individual's response to the environmental factor after accounting for the total usefulness of the predictions overall. It accounts for the utility of the predictions as a whole by evaluating the sign of the residual for each individual of a linear model of change in phenotype on genotype score multiplied by change in environmental factor; a linear regression of the scatter plot shown in FIG. 11B depicts an example graph utilizing simulated data, produced at step 907 in the simulation example of FIG. 9A and FIG. 9B. This graph shows the number of times each locus makes a correct prediction about the sign of this residual based on the reasoning that loci that actually control the response to the environmental factor will influence this residual in the direction indicated by their effect, while the genotype score may be influenced by loci that were statistically significant but do not actually control the response. As such, causal loci will make a correct prediction about the sign of the residual more often than expected by chance, which allows evaluation of each locus used in the predictions individually following an intervention utilizing all candidate GxEs. As expected, in FIG. 11A causal loci (indicated by triangles) make correct predictions about the sign of the residual much more often than non-causal loci (points) even though a number of non-causal loci were flagged as candidate GxEs by the method (to the right of the vertical line on the x-axis, p-value for the test for non-homogeneous regression slopes $<=1*10^{-4}$). 11B shows the loci rank-ordered by number of correction predictions about the sign of the residual, showing that causal loci (triangles) made correct predictions more often than non-causal loci (points), though a small number of causal loci did not outperform non-causal loci.

FIG. 12A depicts a graph with simulated data displaying one possible source of bias in the method, showing the p-value for non-homogeneous regression slopes on the y-axis and the minor allele frequency of each locus valuated on the x-axis; loci with low minor allele frequency experienced inflation of their p-values such that many non-causal loci with minor allele frequencies lower than 0.2 were incorrectly flagged as causal loci. FIG. 12B depicts a graph with simulated data which shows the number of discordant comparisons made in the GxE detection step, which is related to the minor allele frequency but somewhat variable as a result of random selection of individuals for each dyad; loci with low minor allele frequency are likely to have a small number of discordant comparisons, and both conditions are likely to yield false positive results. A preferred embodiment of the method uses a cutoff value of 10,000 discordant dyads based on inflation observed in other simulations. With this cutoff, loci that do not have at least 10,000 discordant dyads are not considered GxEs regardless of their significance because of the inflation of significance observed at sites with smaller numbers of discordant comparisons. The cutoff value is preferentially derived from the extent of tolerance of type I error for the intended use of the method; lower-risk uses can proceed without a cutoff value or with a more permissive value, while higher-risk uses preferentially utilize stringent cutoff values. One embodiment of the method sets this cutoff value at the point at which less than 10% of the loci that are significant, after one or a plurality of multiple testing corrections are performed, are non-causal in a simulation using parameters that approximate the distribution of the source data. Such corrections may include but are not limited to Bonferroni correction, Benjamini-Hochberg correction or others that may be apparently to a practitioner of the art of ordinary skill. To the output shown in FIG. 12B, a value of 20,000 discordant comparisons would optimally be used for the method. Consideration of sources of error in the method is critical in an evidence-based approach to these predictions, and this technique allows a rational estimation of the cutoff parameters to be used in the discovery step based on performance in the simulation.

Some embodiments of the invention implement a method of processing gene-environment interaction information within a data source population, comprising i) Accessing an electronically stored set of genetic information at one or more selected loci that vary in genotype from more than one individual, an electronically stored set of environmental information for at least one selected environmental factor from the more than one individual, and a set of phenotypic information for at least one selected phenotype from the more than one individual;

ii) Processing, using an electronic processing system, the set of genetic information, the set of environmental information, and the set of phenotypic information to: (1) identify genotypes at the one or more selected loci associated with variation in the at least one selected phenotype with variation in the at least one selected environmental factor in inter-individual comparisons (dyads) that have the same genotype at at least one genomic locus evaluated (concordant population) and (2) identify genotypes at the one or more selected loci associated with little or no variation in the at least one selected phenotype with variation in the at least one selected environmental factor in dyads that have the different genotypes at at least one genomic locus evaluated (discordant population); and iii) storing in memory of the electronic processing system genetic information relating the genotypes, the set of environmental information, and the set of phenotypic information.

In some embodiments of the invention, substantial differences between the concordant and discordant populations within the data source population are utilized to indicate the presence of an interaction between an individual's genome and the environment. In some of these embodiments, the phenotypic information is a dependent variable. In some of these embodiments, the genetic information is obtained at a plurality of selected loci. In some of these embodiments, the information in each set is compared between a plurality of individuals in the set. In some of these embodiments, the selected environmental factor is an individual's diet, drug regimen, exercise, surgery, medical care, or geographical location. In some of these embodiments of the invention a signal is detected wherein individuals within a population with the same genotype at one or a plurality of the selected loci are associated with increased variation in the at least one selected phenotype and increased variation in the at least one selected environmental factor. Some of these embodiments further comprise comparing at least the genetic information of a test individual to the data source population, thereby providing a prediction of the phenotype of the test individual. In some of these embodiments of the invention the plurality of individuals do not represent pairs of twins.

Some embodiments of the invention implement a method for processing phenotype, environment, and genotype information, comprising:

i) processing with an electronic data processing system a concordance variance analysis of the phenotype, environment, and genotype information stored in an electronically accessible memory, comprising:

iii) selecting individual-individual comparisons (dyads) to compare at each locus of interest;

iv) calculating a distance in phenotype, environment, and genotype for each dyad of the plurality of dyads; and v) detecting differences in behavior of one or a plurality of populations of dyads with the same genotype at a locus of interest (concordant population) and populations of dyads with a different genotype at a locus of interest (discordant population).

Some embodiments further comprise:

i) data cleaning the phenotype, environment, and genotype information stored in an electronically accessible memory to prepare it for analysis;

ii) selecting a set of phenotypic variables and a set of environmental variables for analysis from the phenotype, environment, and genotype information stored in an electronically accessible memory; and iii) performing heteroscedasticity testing for each phenotype-environment pair.

In some of these embodiments, detecting differences comprises:

i) creating a discordant difference model (DDM) using a machine learning algorithm using discordant dyads where individuals have a different genotype at each locus evaluated; and ii) creating a concordant difference model (CDM) using a machine learning algorithms to create concordant dyads where individuals have the same genotype at the locus evaluated.

In some embodiments of the invention, an optimal number of individual-individual comparisons is determined empirically by evaluating a number of comparisons that most often correctly identifies causal loci.

In some embodiments of the invention, detecting differences comprises:

i) Creating a discordant difference model (DDM) as a linear regression using discordant dyads where individuals have a different genotype at each locus evaluated; and ii) Creating a concordant difference model (CDM) as a linear regression using concordant dyads where individuals have the same genotype at the locus evaluated.

In some embodiments of the invention, differences in any statistical parameters between the DDM and CDM are used as a metric of concordant and discordant comparisons.

Some embodiments of the invention make predictions about one or more new individuals not present in the source data set by extracting loci considered to be involved with gene-environment interactions using a source population at detected sites, then linearly modeling variables for each possible genotype at a each loci of interest. These embodiments then calculate a genotype score for each individual in the dataset based on one or a plurality of their genotypes at loci of interest, sort the source population by genotype score and construct statistical models of the source population for the variables for different ranges of genotype score. They then predict gene-environment interactions of individuals not in the source population based on response of a nearest individuals in the models of the source population.

Some embodiments of the invention include a step wherein, the source population is sorted based on genotype score, and a statistical model for a plurality of segments of the source population segmented by genotype score is constructed.

Some embodiments of the invention include processing system for calculating gene-environment interactions, comprising: data storage to store an input dataset and an output results set, data processing units connected to or incorporating the data storage, computer operable instructions for electronically processing the input dataset, to perform a concordance variance analysis of phenotype, environment, and genotype information stored in an electronically accessible memory comprising:

i) Selecting individual-individual comparisons (dyads) to create a plurality of dyads by random selection of pairs of individuals in a population to compare at each locus of interest;

ii) Calculating differences in phenotype, environment, and genotype for populations of dyads with a different genotype at a locus of interest (discordant population) as well as populations of dyads with the same genotype at a locus of interest (concordant population) for each dyad of the plurality of dyads; and iii) Detecting differences in behavior of concordant and discordant populations.

Some embodiments of the invention, further comprise a screen for displaying one or more aspects of the gene-environment interactions to a user. Some embodiments of the invention are configured to process very large numbers of possible phenotype-environment pairs for large populations.

What is claimed is:

1. A method of processing gene-environment interaction information within a data source population, comprising:
using an electronic processing system connected to data storage and coupled to memory, the data storage storing genetic information, environmental data, and phenotypic data, the processing system executing operations under control of one or a plurality of software programs, the operations comprising accessing the electronically stored set of genetic information at one or more selected loci, an electronically stored set of environmental information for at least one selected environmental factor from more than one individual, and a set of phenotypic information for at least one selected phenotype from the more than one individual;

the operations further comprising processing, using the electronic processing system, the set of genetic information, the set of environmental information, and the set of phenotypic information to: (1) identify inter-individual comparisons (dyads) that have the same genotype at at least one genomic locus evaluated (concordant population) and inter-individual comparisons that have a different genotype at each locus evaluated (discordant population) and (2) calculate the variation between the individuals in each dyad in at least one selected phenotype and the variation between the individuals in each dyad in at least one selected environment;

the processing comprising using a discordant difference machine learning model (DDM) using discordant dyads where individuals have a different genotype at each individual locus evaluated and a concordant difference machine learning model (CDM) in concordant dyads where individuals have the same genotype at each individual locus evaluated; and the operations further comprising storing in memory of the electronic processing system genetic information relating the genotypes, the set of environmental information, and the set of phenotypic information and outputting a representation of predictions of responses of genotype, including an identification of genomic positions related to one or a plurality of phenotype-environment pairs evaluated based on increasing calculated variation in at least one selected phenotype with increasing calculated variation in at least one selected environment in the CDM and statistically significant differences between the CDM and the DDM.

2. The method of claim 1, the operations further comprising determining that differences between the concordant and discordant populations within the data source population indicate the presence of an interaction between an individual's genome and the environment.

3. The method of claim 2 wherein the phenotypic information is a dependent variable.

4. The method of claim 2 wherein the genetic information is obtained at a plurality of selected loci.

5. The method of claim 2 wherein the information in each set is compared between a plurality of individuals in the set.

6. The method of claim 2 wherein the selected environmental factor is an individual's diet, drug regimen, exercise, surgery, medical care, or geographical location.

7. The method of claim 2 wherein individuals within a population with the same genotype at one or a plurality of the selected loci are associated with increased variation in the at least one selected phenotype and increased variation in the at least one selected environmental factor.

8. The method of claim 2 further comprising comparing at least the genetic information of a test individual to the data source population, thereby providing a prediction of the phenotype of the test individual.

9. The method of claim 2 wherein the plurality of individuals represent pairs of twins.

10. A method for processing phenotype, environment, and genotype information, comprising:
with an electronic data processing system that is connected to data storage and coupled to memory, the data storage storing genomic data, environmental data, and phenotypic data, the processing system executing operations under control of one or a plurality of software programs, the operations comprising processing a concordance variance analysis of the phenotype, environment, and genotype information stored in an electronically accessible memory, the concordance variance analysis comprising:
selecting individual-individual comparisons (dyads) to compare at each locus of interest;
calculating a distance in phenotype, environment, and genotype for each dyad of the plurality of dyads; and
detecting differences in behavior of one or a plurality of populations of dyads with the same genotype at a locus of interest (concordant population) and populations of dyads with a different genotype at a locus of interest (discordant population) by creating a discordant difference model (DDM) using a machine learning algorithm using discordant dyads where individuals have a different genotype at each locus evaluated; and creating a concordant difference model (CDM) using a machine learning algorithm to create concordant dyads where individuals have the same genotype at the locus evaluated, testing for non-homogenous regressions between the DDM and CDM and determining a difference in regressions between the DDM and CDM.

11. The method of claim 10, the operations further comprising:
data cleaning the phenotype, environment, and genotype information stored in an electronically accessible memory to prepare it for analysis;
selecting a set of phenotypic variables and a set of environmental variables for analysis from the phenotype, environment, and genotype information stored in an electronically accessible memory; and
performing heteroscedasticity testing for each phenotype-environment pair.

12. The method of claim 10, wherein an optimal number of individual-individual comparisons are determined empirically by evaluating a number of comparisons that most often correctly identifies causal loci.

13. The method of claim 10, wherein detecting differences comprises:
creating a discordant difference model (DDM) as a linear regression using discordant dyads where individuals have a different genotype at each locus evaluated; and
creating a concordant difference model (CDM) as a linear regression using concordant dyads where individuals have the same genotype at the locus evaluated.

14. The method of claim 13, the operations further comprising using differences in any statistical parameters between the DDM and CDM as a metric of concordant and discordant comparisons.

15. The method of claim 10, the operations further comprising:
extracting loci considered to be involved with gene-environment interactions using a source population at detected sites;
linearly modeling variables for each possible genotype at each locus of interest;

calculating a genotype score for each individual in the dataset based on one or a plurality of their genotypes at the loci of interest;

sorting the source population by genotype score;

constructing statistical models of the source population for the variables for different ranges of genotype score; and predicting gene-environment interactions of individuals not in the source population based on response of a nearest individuals in the models of the source population.

16. The method of claim 15, further comprising sorting the source population based on genotype score, and constructing a statistical model for a plurality of segments of the source population segmented by genotype score.

17. The method of claim 10, further comprising outputting a graphical representation of predictions of responses of genotype score groups including a graphical identification of a first predicted response group corresponding to a negative beta value of the DDM and a second predicted response group corresponding to a positive beta value of the CDM, both predicted response groups being associated with p-values of non-homogeneous regression slopes being below a threshold p-value.

18. A processing system for calculating gene-environment interactions, comprising:
   data storage to store an input dataset and an output results set and genomic information, environmental data, and phenotypic data;
   data processing units connected to or incorporating the data storage; and
   memory coupled to the data processing units and storing one or a plurality of software programs with computer operable instructions for electronically processing the input dataset, to perform a concordance variance analysis of phenotype, environment, and the genotype information stored in an electronically accessible memory, the data processing units executing under control of the programs, and the concordance variance analysis comprising:
      selecting individual-individual comparisons (dyads) to create a plurality of dyads by random selection of pairs of individuals in a population to compare at each locus of interest;
      calculating differences in phenotype, environment, and genotype for populations of dyads with a different genotype at a locus of interest (discordant population) as well as populations of dyads with the same genotype at a locus of interest (concordant population) for each dyad of the plurality of dyads; and
      detecting differences in the relationship between at least one selected phenotype and at least one selected environment of one or a plurality of populations of dyads with the same genotype at a locus of interest (concordant population) and populations of dyads with a different genotype at a locus of interest (discordant population) by creating a discordant difference model (DDM) using a machine learning algorithm using discordant dyads where individuals have a different genotype at each locus evaluated; and creating a concordant difference model (CDM) using a machine learning algorithm to create concordant dyads where individuals have the same genotype at the locus evaluated, testing for non-homogenous regressions between the DDM and CDM and determining a difference in regressions between the DDM and CDM.

19. The processing system of claim 18, further comprising a screen for displaying one or more aspects of the gene-environment interactions to a user.

20. The processing system of claim 18, configured to process very large numbers of possible phenotype-environment pairs for large populations.

21. The processing system of claim 18, the software programs further comprising computer operable instructions for outputting a graphical representation of predictions of responses of genotype score groups including a graphical identification of a first predicted response group corresponding to a negative beta value of the DDM and a second predicted response group corresponding to a positive beta value of the CDM, both predicted response groups being associated with p-values of non-homogeneous regression slopes being below a threshold p-value.

* * * * *